US008936795B2

(12) United States Patent
Golzarian et al.

(10) Patent No.: US 8,936,795 B2
(45) Date of Patent: Jan. 20, 2015

(54) LIQUID EMBOLIC MATERIAL INCLUDING CARBOXYMETHYL CHITOSAN CROSSLINKED WITH CARBOXYMETHYL CELLULOSE

(71) Applicant: Regents of the University of Minnesota, St. Paul, MN (US)

(72) Inventors: Jafar Golzarian, Plymouth, MN (US); Lihui Weng, Woodbury, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 14 days.

(21) Appl. No.: 13/720,135

(22) Filed: Dec. 19, 2012

(65) Prior Publication Data

US 2014/0171907 A1  Jun. 19, 2014

(51) Int. Cl.

| | |
|---|---|
| *A61M 5/178* | (2006.01) |
| *A61M 25/00* | (2006.01) |
| *A61L 24/04* | (2006.01) |
| *A61M 5/19* | (2006.01) |
| *A61L 31/04* | (2006.01) |
| *A61L 31/14* | (2006.01) |
| *A61L 31/16* | (2006.01) |
| *A61L 31/18* | (2006.01) |

(52) U.S. Cl.
CPC .............. *A61L 24/043* (2013.01); *A61M 5/178* (2013.01); *A61M 5/19* (2013.01); *A61L 31/041* (2013.01); *A61L 31/145* (2013.01); *A61L 31/16* (2013.01); *A61L 31/18* (2013.01)
USPC ........... 424/400; 604/508; 604/264; 604/187; 206/219; 514/781; 514/34; 514/152

(58) Field of Classification Search
None
See application file for complete search history.

(56) References Cited

U.S. PATENT DOCUMENTS

| | | | |
|---|---|---|---|
| 5,635,215 | A | 6/1997 | Boschetti et al. |
| 5,648,100 | A | 7/1997 | Boschetti et al. |
| 7,407,646 | B2 | 8/2008 | Laurent et al. |
| 2004/0071776 | A1 | 4/2004 | Boudy et al. |
| 2005/0263916 | A1 | 12/2005 | Lanphere et al. |
| 2006/0105014 | A1* | 5/2006 | Cruise .......................... 424/423 |
| 2006/0199010 | A1 | 9/2006 | DiCarlo et al. |
| 2006/0210635 | A1 | 9/2006 | Laurent et al. |
| 2007/0031467 | A1 | 2/2007 | Abrahams et al. |
| 2008/0039890 | A1* | 2/2008 | Matson et al. ................. 606/200 |
| 2008/0041715 | A1 | 2/2008 | Lanphere et al. |
| 2009/0117196 | A1 | 5/2009 | Boschetti |
| 2011/0082427 | A1* | 4/2011 | Golzarian et al. ............ 604/187 |

FOREIGN PATENT DOCUMENTS

| | | |
|---|---|---|
| EP | 1508344 A1 | 2/2005 |
| WO | 2009072146 A1 | 6/2009 |

OTHER PUBLICATIONS

Shi et al., "Therapeutic Embolization of Meningiomas with Onyx for Delayed Surgical Resection," Surgical Neurology, Nov. 2008, 70:478-481 (Epublished Feb. 8, 2008).
Pollak et al., "The Use of Cyanoacrylate Adhesives in Peripheral Embolization," Journal of Vasc Interv Radiol, Aug. 2001, 12:907-913.
Barnett et al., "In Vitro Assessment of EmboGel and UltraGel Radiopaque Hydrogels for the Endovascular Treatment of Aneurysms," Journal of Vasc Interv Radiol, Apr. 2009, 20:507-512.
Silas et al., "Sclerosis of Postoperative Lymphoceles: Avoidance of Prolonged Catheter Drainage with Use of a Fibrin Sealant," Journal of Vasc Interv Radiol, Nov. 2006, 17:1791-1795.
Ko et al., "Preoperative Portal Vein Embolization with a New Liquid Embolic Agent," Radiology, May 2003, vol. 227, No. 2:407-413 (Epublished Mar. 13, 2003).
Fatimi et al., "A New Injectable Radiopaque Chitosan-Based Sclerosing Embolizing Hydrogel for Endovascular Therapies," Acta Biomaterialia, Jul. 2012; 8(7):2712-21 (Epublished Apr. 7, 2012).
Brennecka et al., "In Vivo Experimental Aneurysm Embolization in a Swine Model with a Liquid-to-Solid Gelling Polymer System: Initial Biocompatibility and Delivery Strategy Analysis," World Neurosurgery, Nov. 2012; 78 (5):469-80 (Epublished Nov. 1, 2011).
Su et al., "Histopathological studies of a New Liquid Embolization Method Using Estrogen-Alcohol and Polyvinyl Acetate: Experimental Evaluations with a Model of Cortical Arterial Cannulation in the Canine Brain," Surgical Neurology, Jul. 1991, vol. 36, No. 1:4-11.
Mottu et al., "Iodine-Containing Cellulose Mixed Esters as Radiopaque Polymers for Direct Emoblization of Cerebral Aneurysms and Arteriovenous Malformations," Biomaterials, Jan. 2002, 23(1):121-131.
Kutlu et al, "Pulmonary Embolism After Penile Deep Dorsal Vein Embolization with n-butyl-2-cyanoacrylate and Lipiodol Mixture" Eur Journal Radiol Extra, Mar. 2004, 49(3):103-106.
Kazekawa et al., "Newly Synthesized Liquid Embolization Material for Arteriovenous Malformation," Journal Clinical Neurosci, Mar. 1998, 5:45-48.

(Continued)

*Primary Examiner* — Robert A Wax
*Assistant Examiner* — Danah Al-Awadi
(74) *Attorney, Agent, or Firm* — Shumaker & Sieffert, P.A.

(57) ABSTRACT

A liquid embolic material may include a mixture of a first solution comprising between about 1.2% and about 2.5% weight per volume (w/v) carboxymethyl chitosan (CCN) in a first solvent and a second solution comprising between about 1.2% and about 2.5% w/v oxidized carboxymethyl cellulose (OCMC) in a second solvent. The liquid embolic material may be used to embolize a targeted embolization location by mixing the first solution and the second solution to form a liquid embolic material (or hydrogel precursor material), introducing the hydrogel precursor material to a targeted embolization location within a body of a patient, and allowing the CCN and the OCMC to react to form the hydrogel material and embolize the targeted embolization location.

29 Claims, 11 Drawing Sheets

(56) References Cited

OTHER PUBLICATIONS

Weng et al., "In Vitro Assessment of an in Situ Gelable Hydrogel for Adjunct Endovascular Treatment of Abdominal Aortic Aneurysms," Journal of Vascular and Interventional Radiology, Abstract 346, Mar. 2012, 23(3): S139.

Kettenbach et al. "Drug-Loaded Microspheres for the Treatment of Liver Cancer: Review of Current Results", Cardiovasc Intervent Radiol (2008) 31:468-476 (Epublished Jan. 29, 2008).

Laurent, "Microspheres and Nonspherical Particles for Embolization," Techniques in Vascular and Interventional Radiology, vol. 10, No. 4, Dec. 1, 2007, pp. 248-256.

Ohta et al., "Degradable Gelatin Microspheres as an Embolic Agent: An Experimental Study in a Rabbit Renal Model," Korean J. Radiol 8(5), Oct. 2007, pp. 418-428.

Nitta et al., "Gelatin Microspheres: Initial Clinical Experience for the Transcatheter Arterial Embolization," European Journal of Radiology, vol. 67, Issue 3, Sep. 2008, 536-540.

Wang et al., "Preparation and Characterization of Pingyangmycin-loaded Bovine Serum Albumin Microspheres for Embolization Therapy," International Journal of Pharmaceutics, vol. 336, No. 2, May 24, 2007, pp. 361-366.

Laccourreye et al., "Biodegradable Starch Microspheres for Cerebral Arterial Embolization," Journal of Clinical and Laboratory Research, vol. 28, No. 2, Feb. 1993, pp. 150-154.

Flandroy et al., "(D,L) Polylactide Microspheres as Embolic Agent," Neuroradiology, vol. 32, No. 4, Feb. 1990, pp. 311-315.

Wu et al., "Preparation and Drug Release Characteristics of Pingyangmycin-Loaded Dextran Cross-Linked Gelatin Microspheres for Embolization Therapy," Journal of Biomedical Materials Research, Part B, vol. 78B, Issue I, Jul. 2006, 56-62.

Liu et al., "A Study of Doxorubicin Loading Onto and Release from Sulfopropyl Dextran Ion-Exchange Microspheres," Journal of Controlled Release, vol. 77, Dec. 2001, pp. 213-224.

* cited by examiner

FIG. 5A
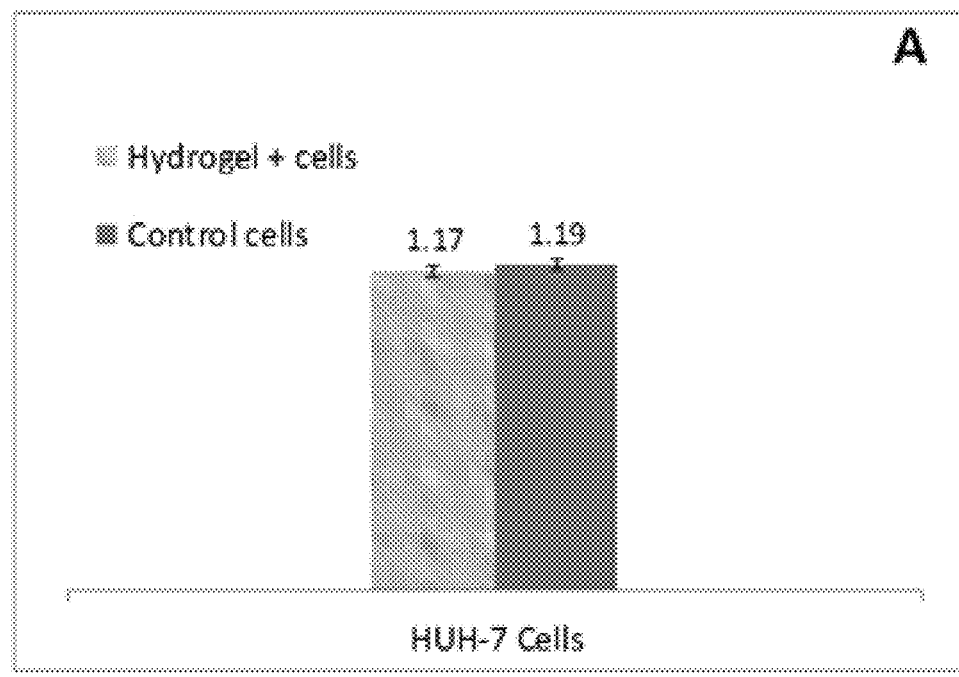
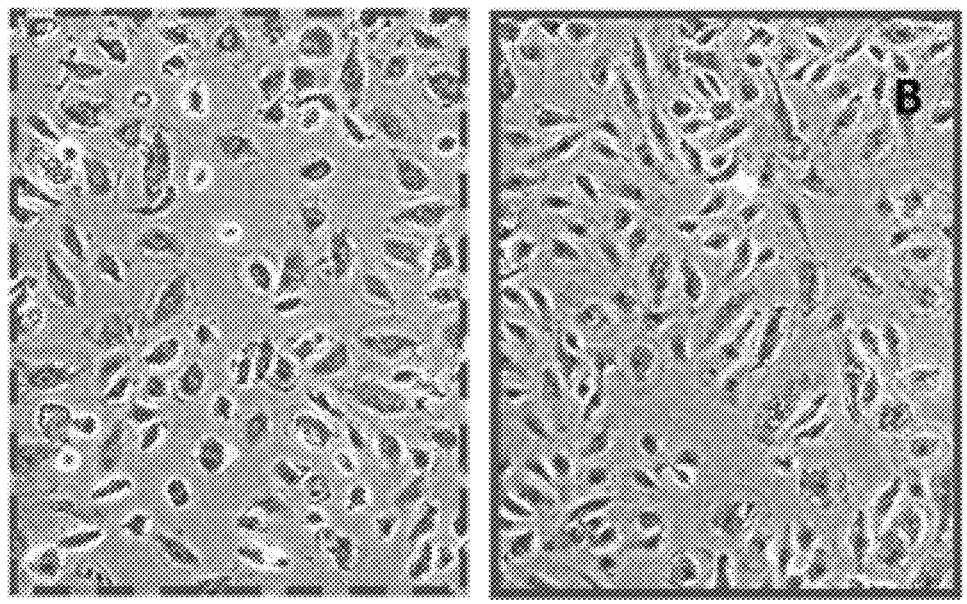
FIG. 5B

LIQUID EMBOLIC MATERIAL INCLUDING CARBOXYMETHYL CHITOSAN CROSSLINKED WITH CARBOXYMETHYL CELLULOSE

TECHNICAL FIELD

The disclosure relates to embolic materials.

BACKGROUND

Embolization has been widely accepted for its efficacy in treating various diseases including tumors, vascular lesions, and hemorrhages. For a safe and effective treatment, the selection of an appropriate embolic material is important. Liquid embolic materials may include ethanol; a mixture of ethylene vinyl alcohol copolymer dissolved in dimethyl sulfoxide (DMSO) and opacified with tantalum powder (available under the trade designation Onyx, from Covidien, Mansfield, Mass.); detergents, such as morrhuate sodium, or sotradecol; and cyanoacrylate. Liquid embolic materials such as ethanol, Onyx, and detergents can easily pass through capillaries, causing distal embolization or untargeted embolization. Cyanoacrylate is a non-resorbable tissue glue, which requires careful assessment of the proper dilution and control of vascular penetration due to its strong adhesion to tissue.

SUMMARY

The disclosure describes embolic materials comprising carboxymethyl chitosan (CCN) crosslinked with carboxymethyl cellulose (CMC). The embolic materials described herein can be delivered to a target region in liquid form and gel in-situ (e.g., in vivo). For example, CCN can be dissolved in a first solvent and oxidized CMC (OCMC) can be dissolved in a second solvent. The first and second solvents (including the CCN and the OCMC) can be mixed at the time of injection or just before delivery to the target region. The CCN and the OCMC may begin crosslinking (forming a hydrogel) upon mixing, but the crosslinking reaction does not complete instantaneously. Hence, the liquid mixture in which the crosslinking reaction is occurring may flow to the target region prior to completion of the crosslinking reaction. The time from initial mixing to substantial completion of the crosslinking reaction may be influenced by the concentration of CCN and OCMC in the respective first and second solvents.

In some examples, one or both of the first and second solvents may include at least one additional component. For example, the first and/or second solvents may include contrast and/or at least one drug (e.g., pharmaceutical). In this way, the embolic hydrogel may be used to deliver drugs to a location while embolizing the location and/or may be used as a radiopaque marker.

In some examples, the crosslinking reaction between the CCN and OCMC may proceed without use of a small molecule crosslinking agent. Because of this, the embolic hydrogel is expected to be biodegradable and biocompatible.

In one aspect, the disclosure describes a liquid embolic material that includes a mixture of a first solution comprising between about 1.0% and about 2.5% weight per volume (w/v) CCN in a first solvent and a second solution comprising between about 1.0% and about 2.5% w/v OCMC in a second solvent.

In another aspect, the disclosure describes a kit that includes a first container containing a first solution comprising a first solvent and between about 1.0% and about 2.5% w/v CCN, and a second container containing a second solution comprising a second solvent and between about 1.0% and about 2.5% w/v OCMC.

In a further aspect, the disclosure describes a method of making an embolic hydrogel material. The method may include mixing a first solution comprising between about 1.0% and about 2.5% w/v CCN in a first solvent and a second solution comprising between about 1.0% and about 2.5% w/v OCMC in a second solvent to form a hydrogel precursor material, and allowing the CCN and the OCMC to react to form the hydrogel material.

In an additional aspect, the disclosure describes a method including mixing a first solution comprising between about 1.0% and about 2.5% w/v CCN in a first solvent and a second solution comprising between about 1.0% and about 2.5% w/v OCMC in a second solvent to form a hydrogel precursor material, introducing the hydrogel precursor material to a targeted embolization location within a body of a patient, and allowing the CCN and the OCMC to react to form the hydrogel material and embolize the targeted embolization location.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIG. 5A is a bar diagram illustrating an example comparison of cell viability in the presence and absence of a CCN/OCMC hydrogel.

FIG. 5B illustrates two example images, one of cells co-cultured with hydrogel and one of cells cultured without hydrogel.

DETAILED DESCRIPTION

The disclosure describes embolic materials comprising carboxymethyl chitosan (CCN) crosslinked with carboxymethyl cellulose (CMC). Although referred to herein as embolic materials, the materials described herein may be used in other applications, such as for filling a pleural space or intraabdominal cavity. In this way, the embolic materials described herein may also be used as filling materials for cavities. The embolic materials described herein can be delivered to a target region in liquid form and gel in-situ (e.g., in vivo). For example, CCN can be dissolved in a first solvent and partially oxidized CMC (OCMC) can be dissolved in a second solvent. The first and second solvents (including the CCN and the OCMC) can be mixed at the time of injection or just before delivery to the target region. The CCN and the OCMC may begin crosslinking (forming a hydrogel) upon mixing, but the crosslinking reaction does not complete instantaneously. Hence, the liquid mixture in which the crosslinking reaction is occurring may flow to the target region prior to completion of the crosslinking reaction. The time from initial mixing to substantial completion of the crosslinking reaction may be influenced by the concentration of CCN and OCMC in the respective first and second solvents.

CCN is substantially non-toxic and biodegradable. Chitosan breaks down in the body to glucosamine, which can be substantially completely absorbed by a patient's body. Similarly, CMC is substantially non-toxic and biodegradable. Thus a crosslinked polymer formed by CCN and OCMC is expected to the substantially non-toxic (i.e., biocompatible) and biodegradable (or bioresorbable).

The embolic hydrogel formed by in situ gelation of CCN and OCMC may be used in a variety of applications, including applications for which solid or pre-gelled embolic materials, such as embolic microspheres, are less suited. For example, because the embolic hydrogel is introduced into the human body in liquid form before gelling in vitro, the liquid may advance further distally into a blood vessel, e.g., to portions of the blood vessel that have smaller cross-sectional areas, compared to other embolic materials such as microspheres. As another example, the embolic hydrogel may be used to fill a cavity within a body of a patient. The embolic hydrogel may be used in application such as adjunct prevention of endoleakage of abdominal aortic aneurysm (AAA) or as a sclerosing agent to treat lymphocele, varicose vein, or pleural effusion.

Figure 1:
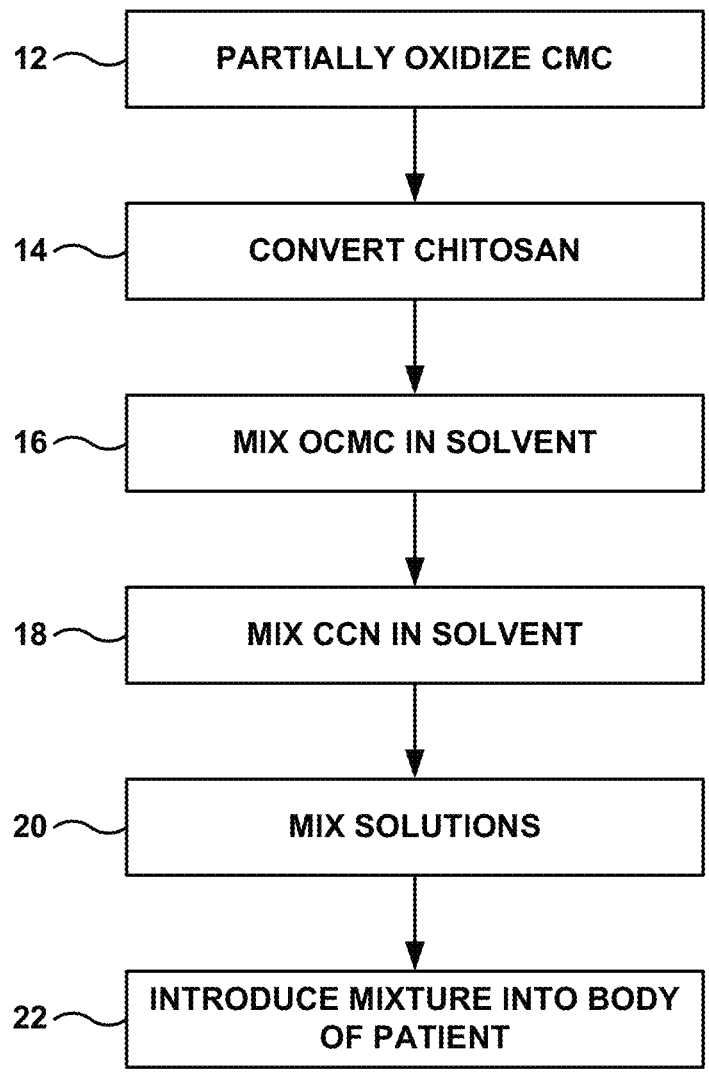
FIG. 1 is a flow diagram that illustrates an example technique for in situ formation of an embolic hydrogel from CCN and OCMC.

FIG. 1 is a flow diagram that illustrates an example technique for in situ formation of an embolic hydrogel from CCN and OCMC. The technique includes at least partially oxidizing CMC to form OCMC (12). One reaction that at least partially oxidizes CMC is illustrated in Reaction 1:

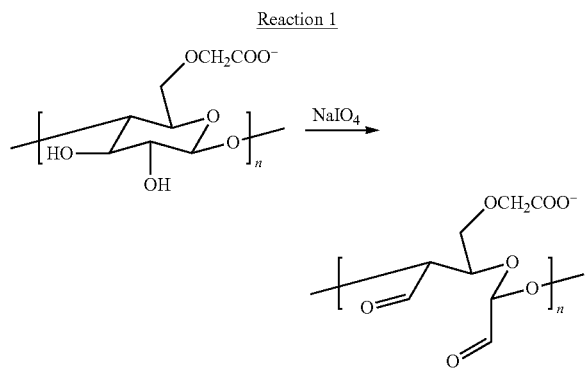

In Reaction 1, a single CMC monomer (repeating unit), which is part of a chain comprising n repeating units, is reacted with $NaIO_4$ (sodium periodate). In some examples, the reaction may be carried out at about 25° C. The reaction between a CMC monomer and $NaIO_4$ oxidizes the C—C bond between carbon atoms bonded to hydroxyl groups to form carbonyl (more particularly, aldehyde) groups. Reaction 1 shows only a single repeating unit (one CMC monomer) of the CMC polymer. In some embodiments, not all repeating units within the CMC polymer may be oxidized. For example, some repeating units may not be oxidized at all, and may still include two hydroxyl groups after Reaction 1 is performed. Other monomers may be fully oxidized, and may include two carbonyl groups, as illustrated in Reaction 1.

The degree of oxidation of the CMC may be affected by, for example, the molar ratio of $NaIO_4$ to CMC repeating units. In some embodiments, the molar ratio of $NaIO_4$ molecules to CMC repeating units may be between about 0.1:1 and about 0.5:1 ($NaIO_4$:CMC). Examples of molar ratios of $NaIO_4$ molecules to CMC repeating units include about 0.1:1, about 0.25:1, and about 0.5:1. An increased molar ratio of $NaIO_4$ molecules to CMC repeating units may result in greater oxidation of the CMC, which in turn may lead to greater crosslinking density when CMC is reacted with CCN to form the embolic hydrogel. Conversely, a decreased molar ratio of $NaIO_4$ molecules to CMC repeating units may result in lower oxidation of the CMC, which in turn may lead to lower crosslinking density when CMC is reacted with CCN to form the embolic hydrogel. In some examples, the crosslinking density may be approximately proportional to the degree of oxidation of the CMC. In some embodiments, a greater crosslinking density may lead to greater mechanical strength (e.g., fracture strain) of the embolic hydrogel.

The OCMC may include a weight average molecular weight of between about 50,000 daltons (Da; equivalent to grams per mole (g/mol)) and about 800,000 Da. In some embodiments, a weight average molecular weight of the OCMC may be about 700,000 g/mol.

CCN may be prepared by reacting chitosan to attach —$CH_2COO^-$ groups in place of one of the hydrogen atoms in an amine group or a hydroxyl group, as illustrated in Reaction 2 (14).

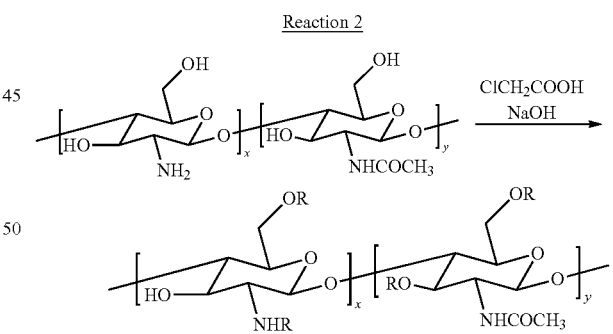

The reactant supplying the —CH2COO$^-$ may include, for example, monochloroacetic acid. In the product of Reaction 2, each R is independently either H or —$CH_2COO^-$. Similar to oxidation of CMC shown in Reaction 1, the extent of the addition of the —$CH_2COO^-$ may affect the crosslink density when the CCN is reacted with the partially oxidized CMC to form the embolic hydrogel. In some embodiments, the ratio of x:y may be about 3:1 (i.e., monomers of "x" form about 75% of the chitosan and monomers of "y" form about 25% of the chitosan).

In some examples, Reaction 2 may be performed by stirring the reaction mixture at 500 rpm for about 24 hours at about 25° C., followed by stirring the reaction mixture at 500 rpm for about 4 hours at about 50° C.

In some embodiments, the chitosan starting material may have a molecular weight between about 190,000 g/mol and about 375,000 g/mol.

Once the OCMC and the CCN have been prepared, each is mixed in a respective amount of a solvent, such as water (e.g., distilled water), saline, or PBS (16), (18). For example, 0.1 milligram (mg) of OCMC may be mixed in 5 milliliter (mL) of water to form a first 2% weight/volume (w/v) solution. Similarly, as an example, 0.1 mg of CCN may be mixed in 5 mL of water to form a second 2% w/v solution. The solvent used in the OCMC solution may be the same as or different than the solvent used in the CCN solution.

The OCMC solution and CCN solution may have other concentrations than 2% w/v. In some examples, the solutions may have concentrations of OCMC or CCN, respectively, between about 0.5% w/v and about 3% w/v. In some examples, the concentrations of the OCMC solution and/or the CCN solution may be between about 1.0% w/v and about 2.5% w/v, such as between about 1.2% w/v and about 2.5% w/v, between about 1.2% w/v and about 2.0% w/v, between about 1.5% w/v and about 2.5% w/v, between about 1.5% w/v and about 2.0% w/v, about 1.5% w/v, about 1.8% w/v, or about 2% w/v. The concentration of the OCMC solution may be the same as or different from the concentration of the CCN solution.

In some examples, one or both of the OCMC solution or the CCN solution may include additional components. For example, either or both of the solutions may include at least one drug (e.g., pharmaceutical) and/or contrast. The contrast may be mixed into the solvent (e.g., water, saline, PBS, or the like). The contrast may be mixed to any desired concentration. An example concentration of contrast may be between about 10% (volume of contrast/volume of solvent; v/v) and about 50% v/v, such as, for example, about 20% v/v.

Similarly, at least one drug may be mixed into the OCMC solution and/or the CCN solution at any concentration. In some examples, the concentration of drug may be defined based on the dry composition (e.g., the composition excluding the solvent and contrast). In some examples, the drug may be mixed into the embolic hydrogel in a ratio of up to about 20% drug to dried polymer (on a weight basis; w/w), such as, for example, between about 5% w/w and about 20% w/w, or between about 5% w/w and about 10% w/w, or about 10% w/w, or about 6% w/w.

The drugs may include, for example, one or more hydrophilic drugs, such as one or more positively charged hydrophilic drug. Example drugs include doxorubicin, idarubicin, irinotecan, or tetracycline.

The solutions may be disposed (e.g., stored) in any suitable container. In an example, the OCMC solution and the CCN solution may be disposed in separate syringes. As described below, the syringes may facilitate dispensing of the solutions for mixing of the solutions and/or introduction of the solutions.

The technique also includes mixing the OCMC solution and the CCN solution to form the liquid embolic material (or hydrogel precursor mixture) (20). In some examples, the solutions may not be mixed until shortly before introduction of the liquid embolic material into a body of a patient. The time at which the OCMC solution and the CCN solution are mixed may be selected base at least in part on, for example, a concentration of OCMC in the OCMC solution, a concentration of CCN in the CCN solution, a location of the target embolization area compared to a location of the location at which the liquid embolic material is introduced into the body, or a size of the target embolization area.

Upon mixing the OCMC solution and the CCN solution (20), the reaction shown in Reaction 3 begins. As shown in Reaction 3, an amino group on the CCN may react with an aldehyde group on the OCMC to form a Schiff base (i.e., an N═C double bond) and crosslink the CMC and the CCN.

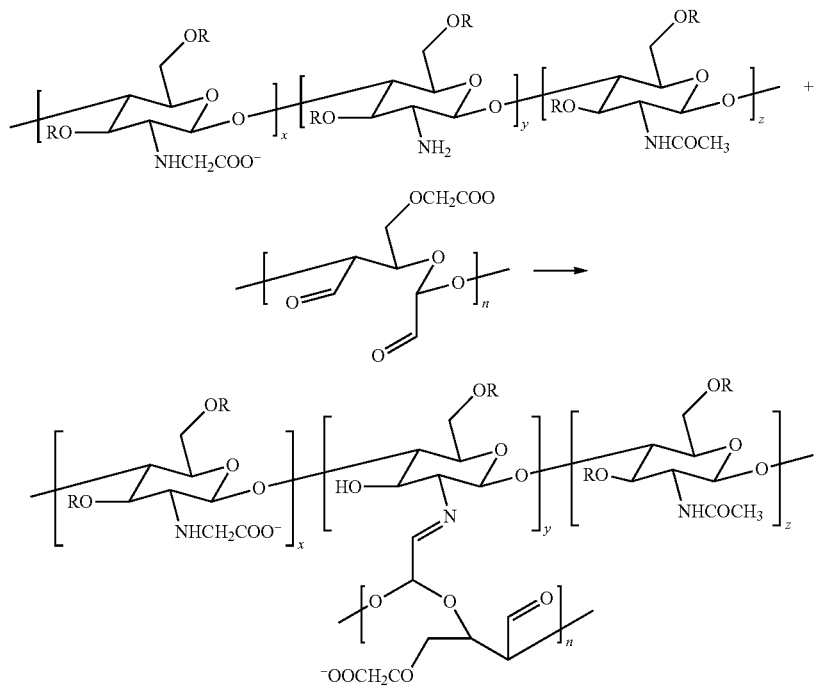

Reaction 3

As discussed above, the crosslinking reaction of the OCMC and CCN may proceed without use of a small-molecule crosslinking agent, such as glutaraldehyde. This may be advantageous, because in some embodiments, a small-molecule crosslinking agent may be toxic to a patient in which the embolic hydrogel is used. In this way, the embolic hydrogel formed from CCN crosslinked with OCMC may be substantially free of any small-molecule crosslinking agent.

In some examples, the crosslinking reaction between OCMC and CCN may proceed under relatively benign conditions. For example, the crosslinking reaction may be carried out at ambient pressures and ambient temperatures (e.g., a temperature within the body of the patient). In some embodiments, a portion of the reaction, e.g., before introduction of the liquid embolic material into the body of the patient, may be carried out at a temperature above ambient, such as, for example, 50° C. Hence, in some examples, a first portion of the reaction may be carried out at a first temperature and/or pressure and a second portion of the reaction may be carried out at a second temperature and/or pressure. Exemplary ranges of temperatures in which the crosslinking reaction may be performed include between about 20° C. and about 70° C., and at about 50° C. and/or about 37° C.

An extent of crosslinking between molecules of OCMC and CCN may affect mechanical properties of the resulting embolic hydrogel. For example, a greater crosslinking density generally may provide greater mechanical strength (e.g., fracture strain), while a lower crosslinking density may provide lower mechanical strength (e.g., fracture strain). The crosslinking density may also affect the degradation rate of the embolic hydrogel. For example, a greater crosslinking density may lead to a longer degradation time, while a lower crosslinking density may lead to a shorter degradation time. In some examples, the crosslink bonds may degrade through hydrolyzing of the C=N double bond.

The OCMC and CCN solutions may be mixed using any suitable technique. One technique for mixing the OCMC solution and the CCN solution includes mixing the OCMC solution and the CCN solution in a container. Another technique for mixing the OCMC solution and the CCN solution includes coupling a first syringe containing the OCMC solution and a second syringe containing the CCN solution to a three-way stopcock valve and mixing the solutions between the two syringes. The OCMC solution and the CCN solution also may be mixed using other techniques.

The OCMC and CCN solutions also may be mixed in any ratio. In some examples, the OCMC solution and the CCN solution may be mixed in a 1:1 ratio, such that equal volumes of OCMC solution and CCN solution are mixed. In other examples, the OCMC solution and the CCN solution may be mixed in a ratio other than 1:1, such that is more OCMC solution or more CCN solution in the hydrogel precursor mixture. Because the CCN mixtures and the OCMC mixtures are mixed, the resulting concentrations of OCMC and CCN in the hydrogel precursor mixture may be lower than the concentration of OCMC in the OCMC solution and the concentration of CCN in the CCN solution. The change in concentration will depend on the respective amounts of OCMC solution and CCN solution, and the concentration of OCMC in the OCMC solution and the concentration of CCN in the CCN solution.

After mixing OCMC solution and the CCN solution to form the hydrogel precursor mixture, the mixture may be introduced into a body of a patient (22). In some instances, the mixture may be introduced into the body of the patient using a microcatheter. The microcatheter may have any of a variety of sizes. As described below, a hydrogel precursor mixture formed from mixing a 2% w/v OCMC solution and a 2% w/v CCN solution may be introduced through a microcatheter having an outer diameter of 3 French (Fr) (and an inner diameter of about 0.027 inch (about 0.6858 millimeter; mm)). In other examples, hydrogel precursor mixtures may be introduced using microcatheters having smaller inner diameters (e.g., 1 Fr or 2 Fr microcatheters), or catheters having larger inner diameters (e.g., greater than 3 Fr microcatheters). Other techniques also can be used to introduce the mixture into a body of a patient, such as transdermal injection using a needle, or the like.

In some examples, the hydrogel precursor mixture may be introduced in the body of the patient proximate to the targeted embolization location. For example, a microcatheter or other introduction device may be advanced within the body of the patient (e.g., within an artery of the patient) proximal to the targeted embolization location. The hydrogel precursor mixture then may be dispensed from the microcatheter and may advance distally to the targeted embolization location, e.g., with the flow of blood in the artery.

In some examples, the location at which the hydrogel precursor mixture is introduced into the body of the patient relative to the targeted embolization location may be selected based at least in part on the concentration of the OCMC and CCN in the hydrogel precursor mixture. For example, hydrogel precursor mixtures with higher concentrations of OCMC and CCN may form a gel more rapidly than hydrogel precursor mixtures with lower concentrations of OCMC and CCN. Accordingly, hydrogel precursor mixtures with higher concentrations of OCMC and CCN may be introduced nearer to the targeted embolization location than hydrogel precursor mixtures with lower concentrations of OCMC and CCN (other conditions being the same or substantially similar). Hydrogel precursor mixtures with lower concentrations of OCMC and CCN may advance more distally in arteries. Other considerations that may influence the determination of where the hydrogel precursor mixture is introduced into the body of the patient may include, for example, a flow rate of bodily fluids (including blood in arteries) at the location where the hydrogel precursor mixture is introduced, a size of the targeted embolization location (e.g., a diameter of the blood vessel to be embolized), or the like.

Similarly, the total amount of hydrogel precursor mixture that is introduced into the body of the patient may be selected based at least in part on a size of the targeted embolization location. For example, a blood vessel having a smaller diameter may require less embolic hydrogel to embolize than a blood vessel having a larger diameter.

In some examples, the liquid embolic material may be provided in a kit. The kit may include a first mixture of OCMC and a first solvent in a first container and a second mixture of CCN and a second solvent in a second container. As described below, the solvent may include, for example, water, saline, or phosphate buffered saline (PBS). In some instances, the kit may additionally include a mixing device, such as a three-way stopcock, and/or an introduction device, such as a needle, a microcatheter, or the like. The kit may facilitate mixing of the first mixture and the second mixture to initiate the reaction between the OCMC and the CCN, followed by introduction of the liquid embolic material to a selected location of a body of a patient.

EXAMPLES

Formation of OCMC and CCN

Sodium carboxymethyl cellulose (CMC) ($M_w$=700,000 Da), chitosan ($M_w$=190,000~310,000 Da), lysozyme (chicken egg white), and tetracycline were purchased from Sigma-Aldrich Corp. (St Louis, Mo.). All the other chemicals and solvents were of highest purity commercially available. OCMC was prepared by oxidizing CMC with sodium periodate. About 1 g of sodium CMC and about 80 mL distilled water were deposited in a 250 mL flask. After the CMC dissolved substantially completely in the distilled water, 25% molar equivalent of sodium periodate in about 20 mL distilled water was added into the flask. The reaction between sodium CMC and sodium priodate was allowed to proceed for about 24 hours at about 25° C. Then, about 0.21 mL ethylene glycol was added into the flask to stop the reaction. After 30 minutes, the reaction mixture was poured into a dialysis tube (MWCO 3500, available from Fisher Scientific, Pittsburgh, Pa.) to dialyze thoroughly against distilled water. Dry product was then obtained by lyophilizing the solution using an OCMC aqueous solution. The oxidation degree of OCMC was defined as the percentage of CMC structural units that were oxidized and it was determined by measuring the aldehyde content in OCMC by iodometry. CCN was synthesized according to a modified method of Chen et al. (Chen X G, Park H J. Chemical characteristics of O-carboxymethyl chitosan related to the preparation conditions. Carbohydr Polym 2003; 53:355-359]. In a 3-neck flask, 2 grams chitosan (available from Sigma-Aldrich, St. Louis, Mo., ≥75% (deacetylated)) was added into a mixture of 16 grams sodium hydroxide, 20 mL distilled water, and 20 mL isopropanol. The mixture was stirred at about 25° C. for about 24 hours. Before carboxymethylation, the contents of the flask were maintained in a water bath at 50° C. for 1 h. Then 16 grams monochloroacetic acid (available from Sigma-Aldrich, St. Louis, Mo.) in 10 mL isopropanol was added dropwise into the reaction mixture. The reaction mixture was stirred at about 50° C. for another 4 hours. The reaction was stopped by adding 80 mL of 70% ethanol. The precipitate was filtered, thoroughly rinsed with 70%-90% ethanol, and vacuum dried at room temperature. The dried product was dissolved in 100 mL water and homogenized for 2 h. The insoluble residue was removed by centrifuging. The supernatant was dialyzed (MWCO 3500, available from Fisher Scientific, Pittsburgh, Pa.) against distilled water extensively followed by lyophilizing the supernatant by freezing the solution at about −20° C. then drying the solution with a freeze-dryer (available from Labconco Corp., Kansas City, Mo.).

In the following examples, data were summarized using mean and standard deviation for numeric variables, and counts and proportions for categorical variables. Student's t test and ANOVA were used for the comparison of means. Difference was considered significant if p was less than 0.05.

Hydrogel Formation and Gelation Time

OCMC aqueous solutions were prepared having OCMC concentrations of 1.5% w/v (grams OCMC per mL solvent), 1.8% w/v, or 2% w/v. CCN aqueous solutions having substantially the same concentrations were also prepared. A hydrogel was prepared by mixing in a 1:1 ratio OCMC and CCN aqueous solutions of similar concentrations OCMC and CCN (e.g., mixing equal volumes of an 1.5% w/v OCMC solution and an 1.5% w/v CCN solution). Once mixed, the hydrogel precursor mixtures were added into 24-well non-tissue culture plates and incubated at 37° C. for 2 hours to reach full gelation.

The gelation time of the CCN/OCMC precursor (sol) with or without contrast (Optiray 320, available from Mallinckrodt, Inc., Hazelwood, Mo.) was determined by mixing about 100 μL of OCMC solution and about 100 μL CCN solution with a magnetic stir bar in a Petri dish (available from Becton, Dickinson and Company (BD), Franklin Lakes, N.J.) at 155 revolutions per minute (rpm) using a hotplate/stirrer (Isotemp 11-100, available from Fisher Scientific, Pittsburgh, Pa.). The gelation time was determined when the mixture formed a globule. The experiments were repeated four times per sample.

Figures 2A, 2B:
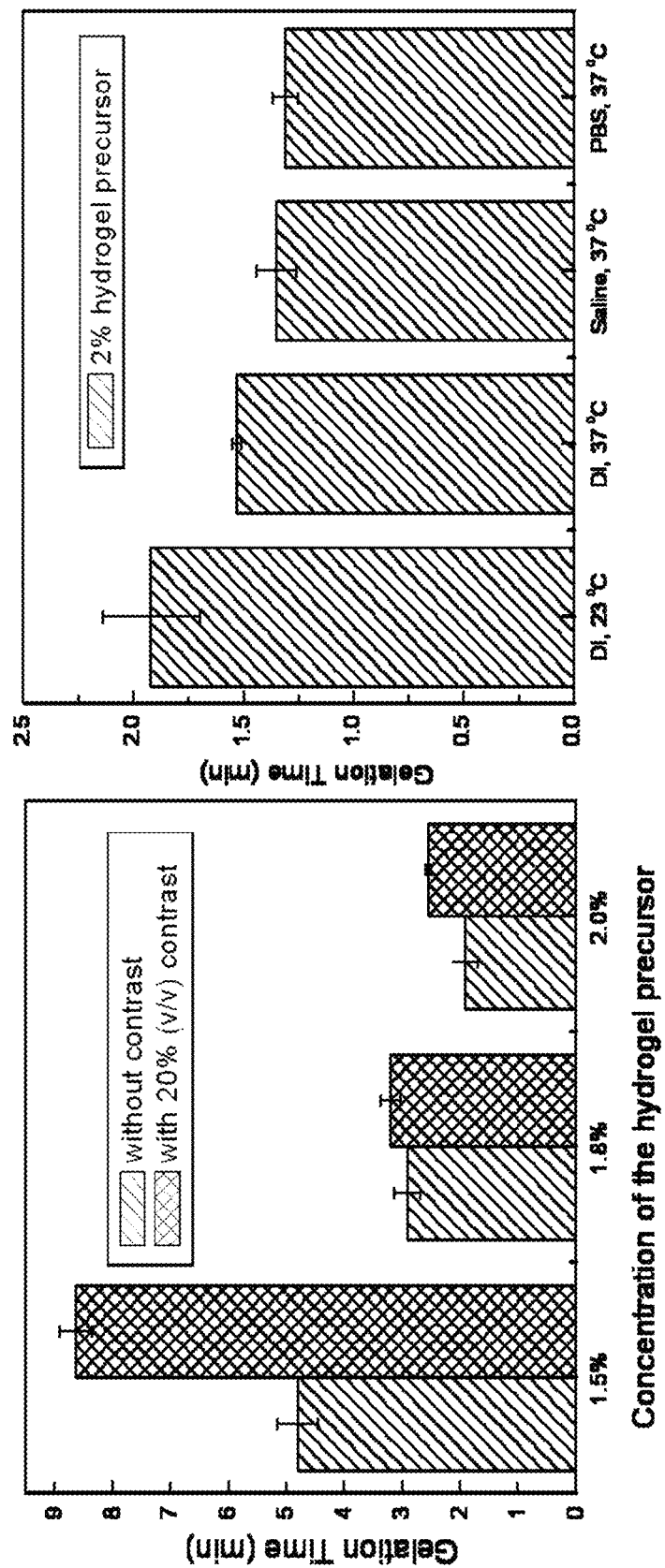
FIGS. 2A and 2B are bar diagrams illustrating example gelation times for hydrogel precursor mixtures having different concentrations, and in different solvents, respectively.

The hydrogel precursor mixture underwent a sol-gel transition and gelled into a clear hydrogel at both ambient temperature (about 23° C.) and 37° C. As shown in FIG. 2A, at 23° C., the gelation time decreased from 4.81±0.35 minutes to 2.91±0.23 minutes to 1.92±0.22 minutes (mean±SD) with an increase in the CCN and OCMC concentration (in the CCN solution and the OCMC solution, respectively mixture) from 1.5% w/v to 1.8% w/v to 2% w/v, as shown in FIG. 2A. Incorporation of iodine contrast delayed the gelation process, but less delay was observed at higher polymer concentrations. For example, in the presence of 20% (v/v) contrast, the hydrogel precursor mixture with 2% w/v CCN and OCMC (concentration defined based on the CCN solution and the OCMC solution, respectively) formed a radiopaque gel within 2.55±0.05 minutes (mean±SD), the hydrogel precursor mixture with 1.8% w/v CCN and OCMC formed a radiopaque gel within 3.2±0.17 minutes, and the hydrogel precursor mixture with 1.5% w/v CCN and OCMC formed a radiopaque gel within 8.63±0.28 minutes. As shown in FIG. 2B, hydrogel precursor mixtures formed of a 1:1 ratio of 2% w/v OCMC solution and 2% w/v CCN solution formed hydrogels in different media, such as distilled water (DI), 0.01 molar (M) PBS, and 0.9% normal saline. At 37° C., gelation in PBS occurred slightly sooner (1.31±0.06 min) than gelation in DI (1.53±0.02 min) or saline (1.35±0.09 min). Elevating the temperature from 23° C. to 37° C. accelerated the gelation process in distilled water from 1.92±0.22 minutes to 1.53±0.02 min.

Gelation of Hydrogel Precursor Mixture in Vial

Figure 3A:
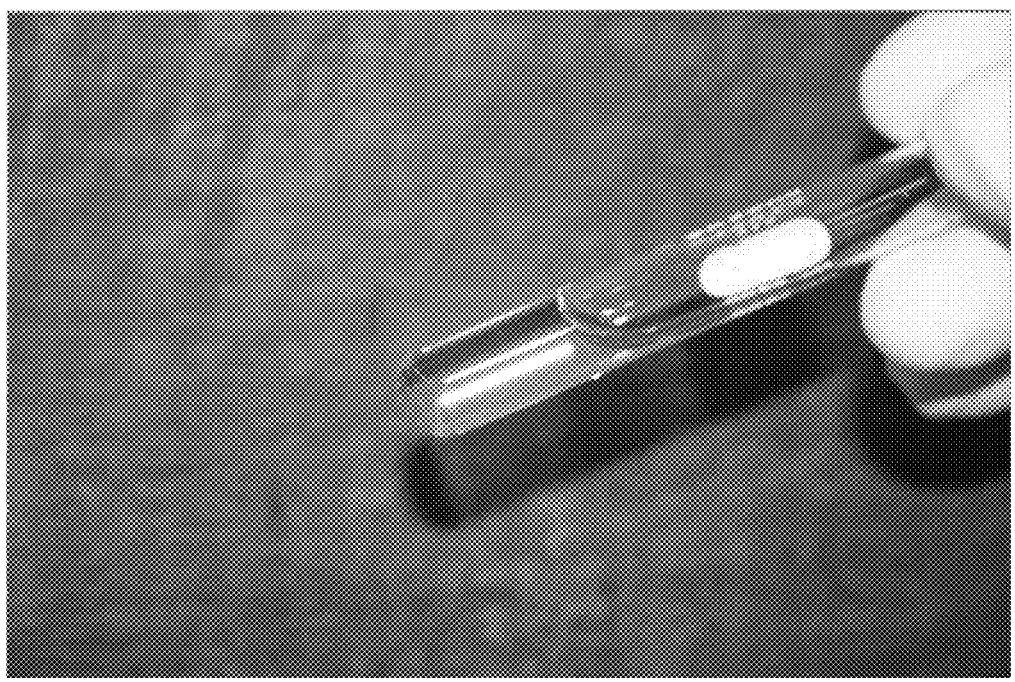
FIGS. 3A and 3B are images of an example hydrogel precursor mixture and a hydrogel embolic material, respectively.
Figure 3B:

FIGS. 3A and 3B are images of an example hydrogel precursor mixture and a hydrogel embolic material in a vial. FIG. 3A shows the hydrogel precursor mixture after mixing an OCMC solution with a CCN solution. The OCMC solution included 2% w/v OCMC in saline. The CCN solution included 2% w/v CCN in saline. FIG. 3B shows the hydrogel embolic material formed by crosslinking of CCN and OCMC after allowing the crosslinking reaction to proceed to completion. As shown in FIG. 3B, the hydrogel possesses sufficient mechanical integrity to maintain its shape when the vial is inverted.

Morphology

The morphology of lyophilized hydrogel was evaluated by scanning electron microscopy (SEM) (JEOL JSM-6700F, available from JEOL Ltd., Tokyo, Japan) after spray-coating the lyophilized hydrogel with gold. Swollen gel pieces were snap-frozen in liquid nitrogen and then lyophilized. A section of the dried gel was mounted on a metal stub coating a layer of conductive adhesive. SEM images were obtained at a 2.0 kV (kilovolt) acceleration voltage in a deceleration mode under a nitrogen atmosphere.

Figure 4:
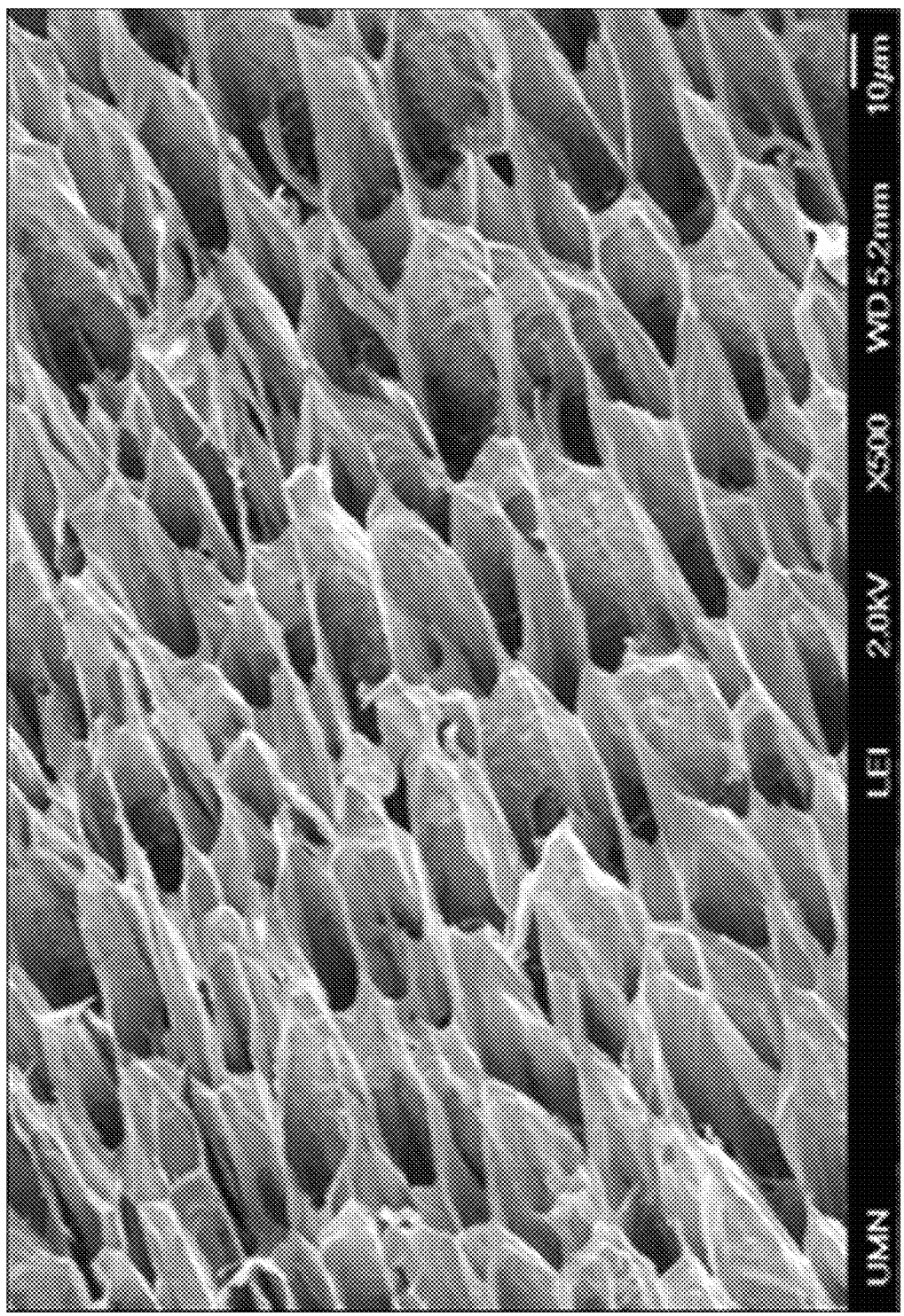
FIG. 4 is an example scanning electron microscopy (SEM) image of an example CCN/OCMC hydrogel.

FIG. 4 is an example SEM image. As shown in FIG. 4, SEM revealed interconnecting pores in the hydrogel prepared from a 2% w/v hydrogel precursor mixture (concentrations based on the OCMC solution and CCN solution before mixing) and pore size analysis gave an average pore diameter of 17±4 μm (mean±SD), demonstrating the possibility of drug diffusion or nutrition exchange through these pores. In addition, it was also observed that the pore size distribution depends on the swollen state of the hydrogel and polymer concentration (data not shown).

Cytotoxicity

Primary human umbilical vein endothelial cells were purchased from VEC Technologies, Inc. (Resselaer, N.Y.). In order to avoid cell damage caused by weight of the hydrogel, one circular piece of plastic was put at the center of each dish before seeding. The endothelial cells were seeded in 35 mm plastic dishes (an area of 8.55 cm$^2$, available from Becton, Dickinson and Company (BD), Franklin Lakes, N.J.) at a density of 200,000 cells per dish. Hydrogels were prepared from a mixture of 2% w/v OCMC solution and 2% w/v CCN solution. The resulting hydrogels were conditioned with PBS solution (10×, pH 7.4, available from Life Technologies Corp., Grand Island, N.Y.) while shaking at 50 strokes/minute for about 30 minutes. Thereafter, the hydrogels were sterilized with 70% v/v ethanol, and thoroughly rinsed with PBS. The hydrogels then were conditioned with standard endothelial cell medium to remove PBS trapped inside the hydrogel. For the study group, the circular plastic piece in the plastic dish was removed after 24 hours and replaced with a piece of hydrogel. After culturing for about 24 hours with and without hydrogel, cells were rinsed twice with HBSS (Hank's Balanced Salt Solution, available from Life Technologies Corp., Grand Island, N.Y.). The cells then were incubated for about 30 minutes in MTT reagent (a tetrazolium dye, available from Sigma-Aldrich, St. Louis, Mo.) diluted in phenol-free 20% Roswell Park Memorial Institute medium at 37° C. Absorbance at 570 nanometers (nm) was determined using a microplate reader (Gen5, available from BioTek® Instruments, Inc., Winooski, Vt.).

The standard MTT assay based on the number of viable cells in the culture dish showed no significant difference between endothelial cells cultured with and without hydrogels (1.17 vs. 1.19, p=0.8, n=4), as shown in the bar diagram of FIG. 5A. There was also no difference in cell viability over time, as the culture period was varied from 24 hours to 72 hours with no difference in cell viability.

FIG. 5B illustrates example images of cells co-cultured with hydrogel and without hydrogel. As shown in FIG. 5B, there were no significant differences in cell density, cell morphology and cell distribution between cells co-cultured with hydrogels (left image of FIG. 5B) and monolayer control, which was cultured without hydrogel (right image of FIG. 5B).

Drug Loading and Release

In vitro drug release experiments were performed using drug loaded hydrogel. Three milliliters (mL) of a 2% w/v CCN aqueous solution, 1 mL 1.2% w/v tetracycline aqueous solution, and 2 mL of 3% w/v OCMC aqueous solution were mixed in a vial. Upon formation of the hydrogel, assuming full reaction of the OCMC and CCN and absorption of all the drug into the hydrogel, the drug payload is about 10% (drug weight per dry hydrogel weight; w/w). After the solutions were mixed well, three 2 mL aliquots were removed from the vial and one aliquot was introduced into each of three 20 mL glass vials. The vials were maintained at about 37° C. for about 2 hours to ensure complete gelation.

Drug release studies were performed at three different pH conditions: 2, 6, and 7.4. Fifteen milliliters of solution at the desired pH was added to a vial containing the hydrogel. The vials (including the hydrogel and the solution) were incubated at 37±0.5° C. with mild shaking (about 100 strokes/min). At predetermined time-points (15 minutes, 30 minutes, 45 minutes, 60 minutes, 2 hours, 3 hours, 4 hours, 5 hours, 6 hours, 8 hours, 10 hours, 24 hours, 32 hours, 48 hours, 56 hours, and 72 hours), 200 µL aliquots were withdrawn from each vial and replaced with an equal volume of fresh medium of similar pH. Absorbance of the released tetracycline was read at a predetermined wavelength ($\lambda_{max}$) with a UV spectrophotometer (Beckman DU650, available from Beckman Coulter, Inc., Brea, Calif.) for each pH sample. Calibration curves were prepared for a series of tetracycline solutions with known concentrations for each pH prior to the conduct of each release study.

Figures 6A, 6B, 6C:
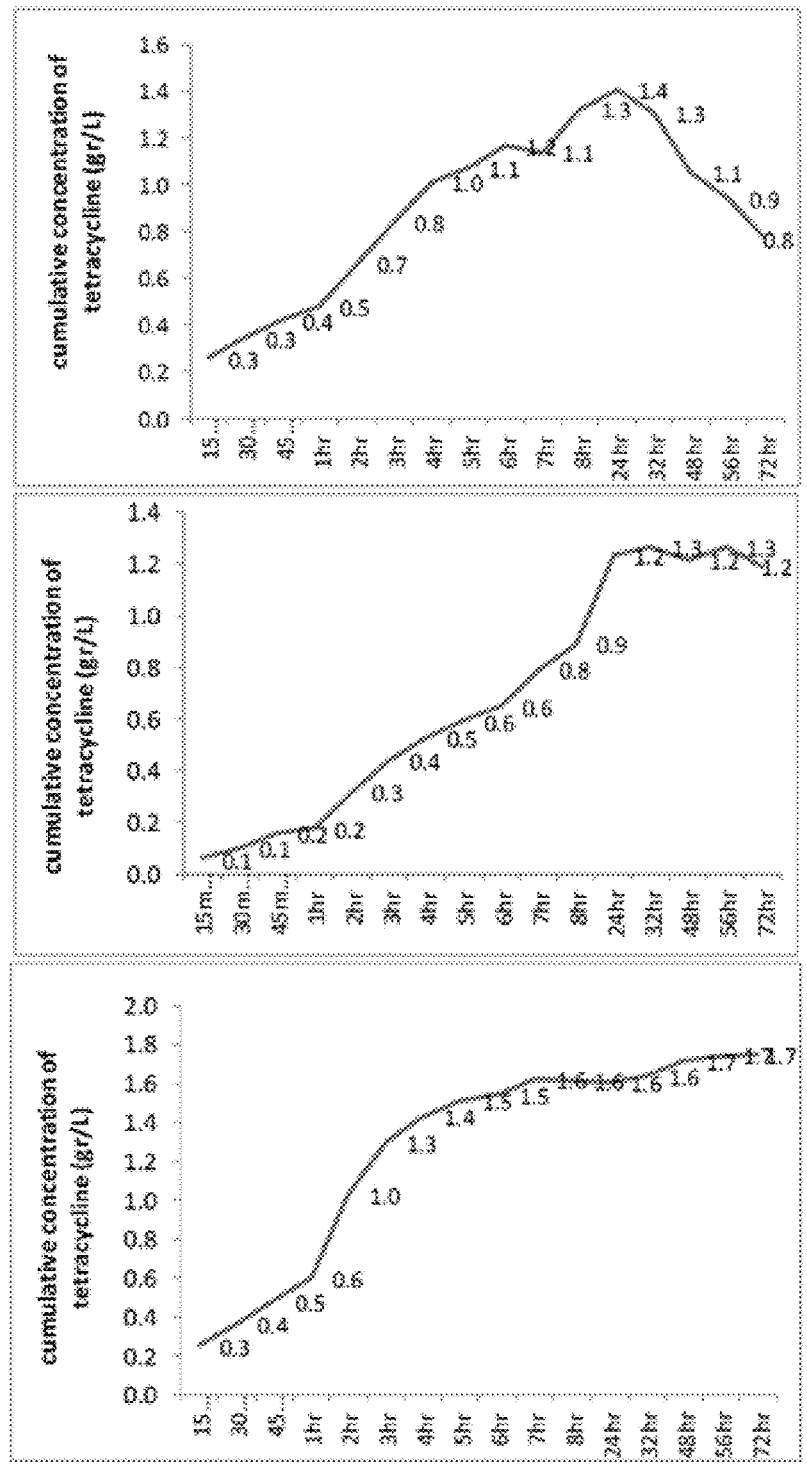
FIGS. 6A-6C are line diagrams illustrating example concentrations of tetracycline in solution over time for solutions of three different pH levels.

FIGS. 6A-6C are line diagrams that illustrate example tetracycline concentrations in a solution for times ranging from 15 minutes to 72 hours. Tetracycline loading was performed during the hydrogel preparation to give a drug payload of about 10% w/w. As shown in FIGS. 6A-6C, the amount of tetracycline in the solution increased over the first 24 hours for all pH levels. As shown in FIG. 6A, the concentration of tetracycline in the pH 7.4 solution declined after 24 hours. On the contrary, in the solution at pH 6 (FIG. 6B) and the solution at pH 2 (FIG. 6C), the tetracycline concentration leveled out after 24 hours, and did not decline before 72 hours.

Enzymatic Degradation

Eighteen pieces of hydrogel were prepared from 0.5 mL 2% w/v OCMC solution and 0.5 mL 2% w/v CCN solution in a 24-well plate for a 30-day period. The hydrogels were incubated with 5 mL of 4 mg/mL lysozyme PBS solution at 37° C. The lysozyme PBS solution was changed every other day (about every 48 hours). At predetermined intervals after beginning the incubation, t, (3, 5, 7, 10, and 12 days), three samples were retrieved and rinsed thoroughly with distilled water. The resulting hydrogel residues were freeze-dried. The percentage of weight loss was calculated based on the following equation: Percent Weight Loss=$[(W_t-W_0)/W_0] \times 100\%$, where $W_t$ and $W_0$ were the dry weight of the hydrogel at day t and day 0, respectively.

Figure 7:
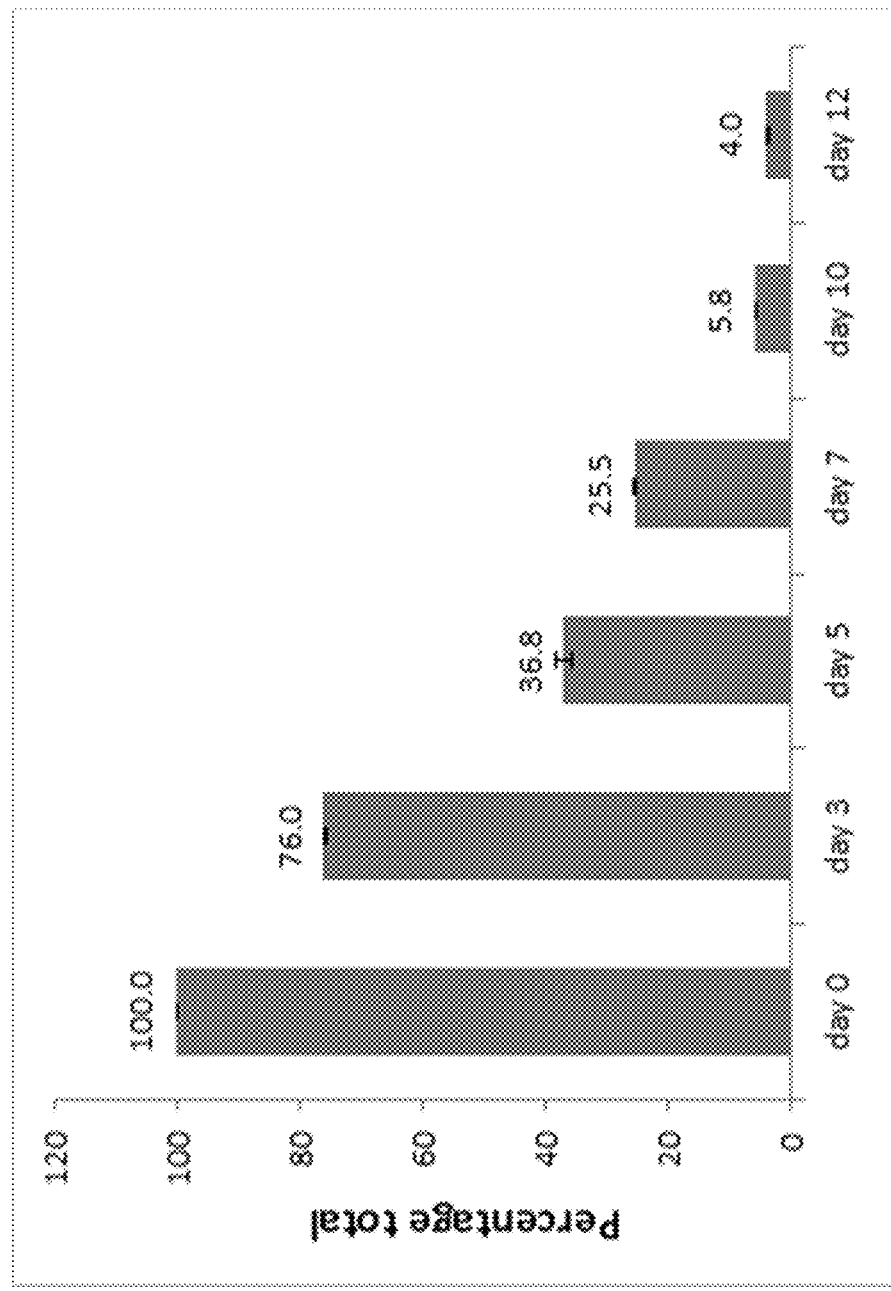
FIG. 7 is a bar diagram illustrating example percentage remaining of a CCN/OCMC hydrogel over time after exposure to lysozyme.

FIG. 7 is a bar graph that illustrates enzymatic degradation of the hydrogel over a period of 12 days. The results shown in FIG. 6 are graphed as percent weight retained (1−Percent Weight Loss or $W_t/W_0 \times 100\%$). As shown in FIG. 6, the dry weight of the hydrogel consistently decreased over the period of incubation with lysozyme. There was a significant drop in remaining hydrogel between day 0 and day 10 (p=0.01). The starting dry weight for the total hydrogel was 20 mg on day 0, and decreased to about 15.2 mg (day 3), about 7.4 mg (day 5), about 5.1 mg (day 7), 1.2 mg (day 10), and 0.8 mg (day 12) demonstrating a consistently decreasing amount of hydrogel, with a decline of more than 20% every two days. The changes after the tenth day were less remarkable, although they remained significant (p=0.01).

Thromboelastography

Human whole blood was collected from one study investigator who was known to have normal results for the assays tested based on previous studies. Blood was collected into a 3.2% sodium citrate vacutainer (available from Becton, Dickinson and Company (BD), Franklin Lakes, N.J.) using routine venopuncture techniques. The blood was kept at room temperature prior to use and testing was initiated between 30 minutes and 2 hours after collection of the blood. Testing was performed on a TEG® Hemostasis System 5000 (available from Haemoscope Corporation, Niles, Ill.). All reagents used were from Haemoscope Corporation, unless noted. Clear disposable TEG® cups and pins were pre-warmed to 37° C. One mL of blood was added to a vial of kaolin and mixed gently by inverting the vial. The reagents for the reaction were placed into the cup in the following order: 320 µL, blood from the kaolin vial, 20 µL saline (0.9% sodium chloride injection USP, available from Baxter Healthcare Corp., Deerfield, Ill.) or hydrogel precursor, and 20 µL 0.2M calcium chloride. The hydrogel precursor was added using a positive-displacement pipette (Microman®, available from Gilson, Inc., Middleton, Wis.). The reaction was allowed to run until all variables had reached their endpoint.

Figure 8:
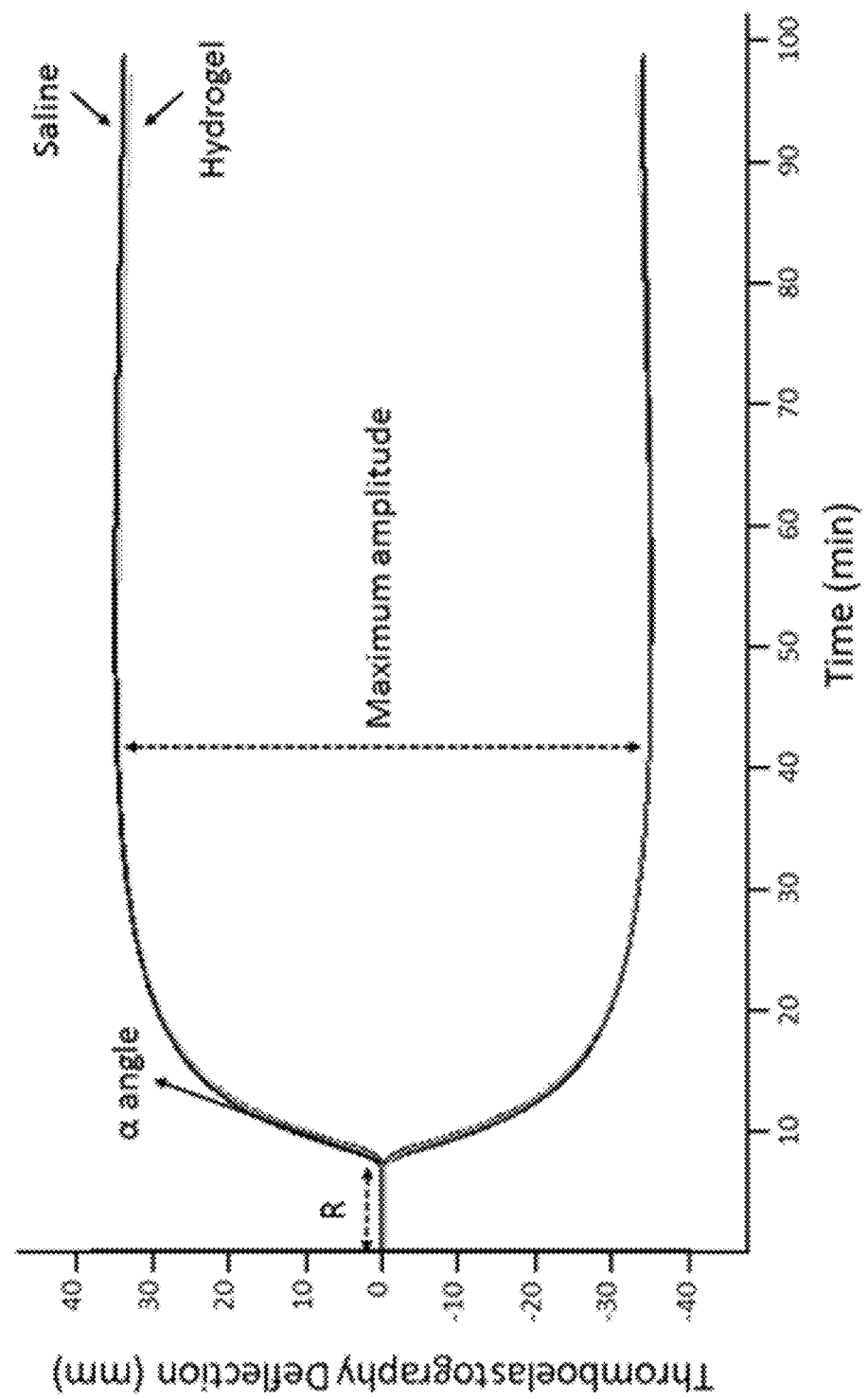
FIG. 8 is a diagram that illustrates example thromboelastographs for citrated whole human blood with normal saline or hydrogel precursor.

FIG. 8 is a diagram that illustrates example thromboelastographs for citrated whole human blood with normal saline or hydrogel precursor. Table 1 shows a summary of the data represented in FIG. 8. Data in Table 1 are expressed as mean±standard deviation (n=4). Together, FIG. 8 and Table 1 summarize the effects of hydrogel gelation on blood coagulation.

TABLE 1

| Sample | R (min) | K (min) | Alpha Angle (deg) | MA (mm) | LY30 (%) | LY60 (%) |
|---|---|---|---|---|---|---|
| Saline | 7.08 ± 0.66 | 2.35 ± 0.66 | 59.05 ± 6.28 | 70.15 ± 1.40 | 0 | 0.05 ± 0.1 |
| Hydrogel | 6.68 ± 0.47 | 2.25 ± 0.58 | 59.38 ± 6.38 | 68.5 ± 1.55 | 0 | 0.23 ± 0.26 |
| p | 0.34 | 0.83 | 0.94 | 0.17 | — | 0.26 |

Significant gelation of the hydrogel precursor did not occur prior to its addition to the reaction. The presence of hydrogel did not have significant effect on the onset of clot formation (R, 7.08 minutes for saline versus 6.68 minutes for hydrogel, p=0.34), coagulation time (K, 2.35 minutes for saline versus 2.25 minutes for hydrogel, p=0.82), or α angle (59.05 degrees for saline versus 59.38 degrees for hydrogel, p=0.94). In addition, there was no significant difference in the clot strength (as measured by the maximum amplitude, MA, 70.15 mm for saline versus 68.5 mm for hydrogel, p=0.17). Similarly, there was no significant different in fibrinolysis at 30 minutes (both were 0%) and 60 minutes (0.05% for saline versus 0.2% for hydrogel, p=0.26).

Injection in an In Vitro Aneurysmal Model

The injectability of a 2% w/v/hydrogel precursor mixture (1:1 mixture of 2% w/v OCMC solution and 2% w/v CCN solution) was tested with a 5 Fr microcatheter (Glidecath, available from Terumo Medical Corporation, Somerset, N.J.; Inner Diameter=0.038 inch (about 0.9652 mm)) after mixing 5 times through a 3-way stopcock. The hydrogel precursor mixture also contained 20% (v/v) contrast. The hydrogel precursor mixture was injected into an aneurysmal sac to assist the endovascular treatment of a fusiform aneurysm model. Fluoroscopy was performed during the procedure depicting the filling of the aneurysmal sac.

Figure 9A:
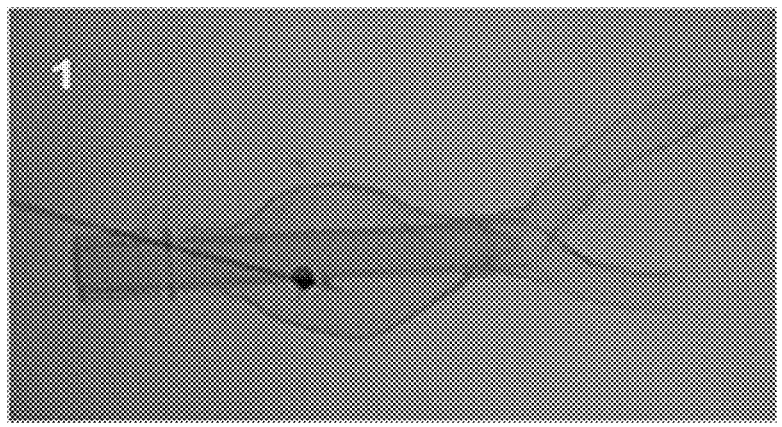
FIGS. 9A-9D are fluoroscopic images that illustrate an example introduction of a hydrogel precursor mixture into a fusiform aneurysmal model.
Figure 9B:
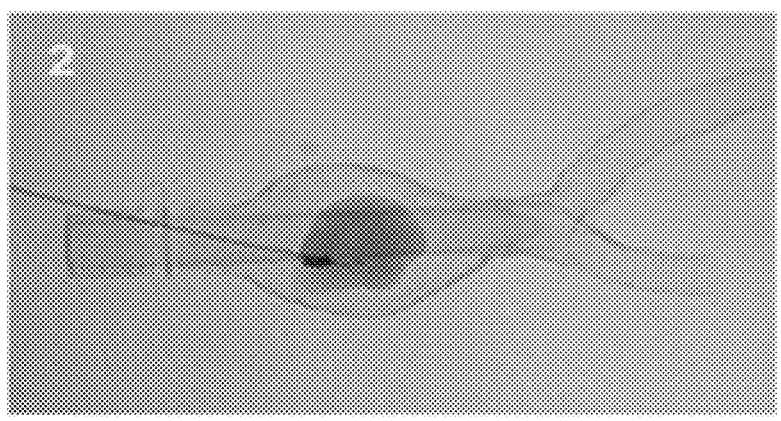
Figure 9C:
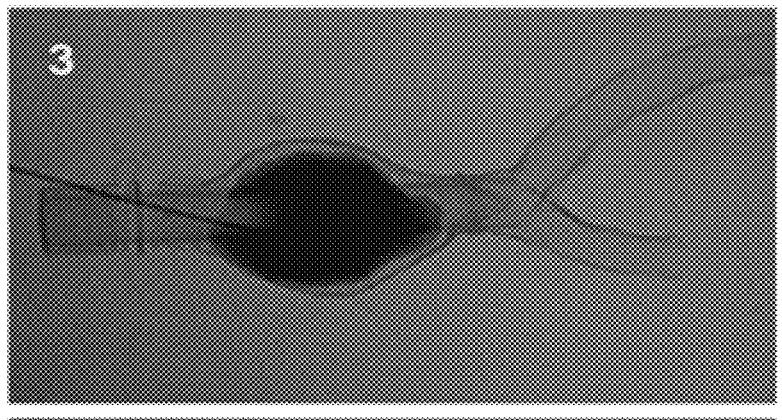
Figure 9D:
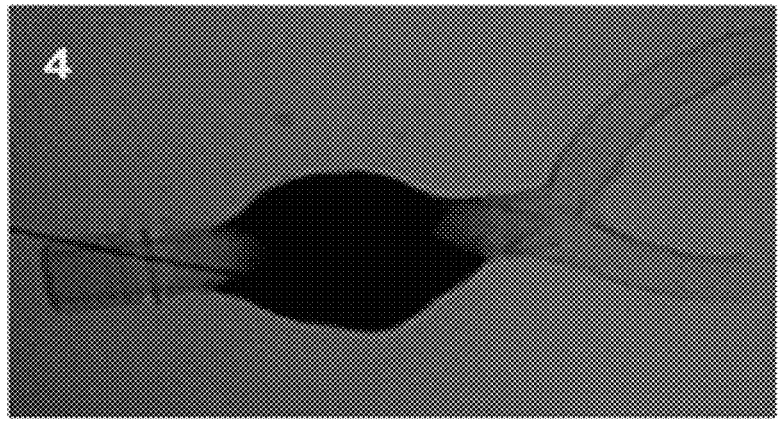

The injection of hydrogel precursors was attempted before the sol transformation into gel. This process was performed under fluoroscopic guidance. FIGS. 9A-9D are fluoroscopic images that illustrate an example of introducing hydrogel precursor mixture into an aneurysmal sac. The contrast allowed visualization of the hydrogel during the process. The hydrogel provided effective embolization in the fusiform aneurysm model, as shown in FIG. 9D. The hydrogel precursor mixture traversed through the 5 Fr microcatheter without any clogging and formed a gel after being introduced into the aneurysm sac. The hydrogel precursor mixture formed a hydrogel in the presence of the ioversol (1-N,3-N-bis(2,3-dihydroxypropyl)-5-[2-hydroxy-N-(2-hydroxyethyl)acetamido]-2,4,6-triiodobenzene-1,3-dicarboxamide) contrast medium (Optiray 320, available from Mallinckrodt, Inc., Hazelwood, Mo.) and was clearly visualized. The gel was able to effectively fill the aneurysmal sac.

Level of Occlusion in Rabbit Renal Model

Four adult rabbits (New Zealand, 2.9 to 3.3 kg) were used. Bioresorbable hydrogel microspheres (diameters between about 100 and about 300 μm), prepared from carboxymethyl chitosan (CCN) and oxidized carboxymethyl cellulose (OCMC, 25% theoretical oxidation degree), were delivered with a 3 French microcatheter to the left kidney of each rabbit at a rate of 1 mL/minute until total occlusion was reached. Two of the right kidneys were embolized with 1.8% w/v CCN/OCMC hydrogel precursor mixture (1.8% w/v based on the concentration of the CCN solution and the OCMC solution), while the other two were embolized with 2.1% w/v hydrogel precursor mixture (2.1% w/v based on the concentration of the CCN solution and the OCMC solution). Animals were euthanized and coronal sections (4 μm in thickness) of the kidneys were obtained for histological staining with hematoxylin and eosin (H&E stain). The location of the microspheres, the deformation of the microspheres and the vessel diameter were analyzed. The deformation of the microspheres was expressed by roundness (as compared to a perfect circle with a roundness of 1) and deformation percentage (D %=100*($D_{max}$-$D_{min}$)/($D_{max}$+$D_{min}$), where $D_{max}$ and $D_{min}$ were the maximum and minimum diameter of the occluded vessel). For hydrogels, the numbers of glomeruli from 6 representative slides were counted for each kidney to obtain the percentage of glomeruli containing hydrogel.

The microspheres were mainly located in interlobar (77.8%) and arcuate arteries (22.2%). The mean (±SD) roundness of the microspheres was 1.02±0.03 and their mean (±SD) deformation percentage was 8.10±5.4%. The mean diameter of the vessel occluded by the microspheres was 224.0 μm.

For the kidneys embolized with 1.8% w/v hydrogel precursor mixture, hydrogel was observed mainly at the glomerular level with a percentage of about 49.2% of 1869 glomeruli counted. For the kidneys embolized with 2.1% w/v hydrogel precursor mixture, hydrogel was found at all levels from interlobar arteries to glomeruli. About 74.9% of the 1907 glomeruli counted were noticed to contain hydrogel. This suggests that hydrogel can occlude location more distal than the microspheres in the vascular network.

Dispensing Hydrogel Precursor Mixture Through Microcatheter

Figure 10A:
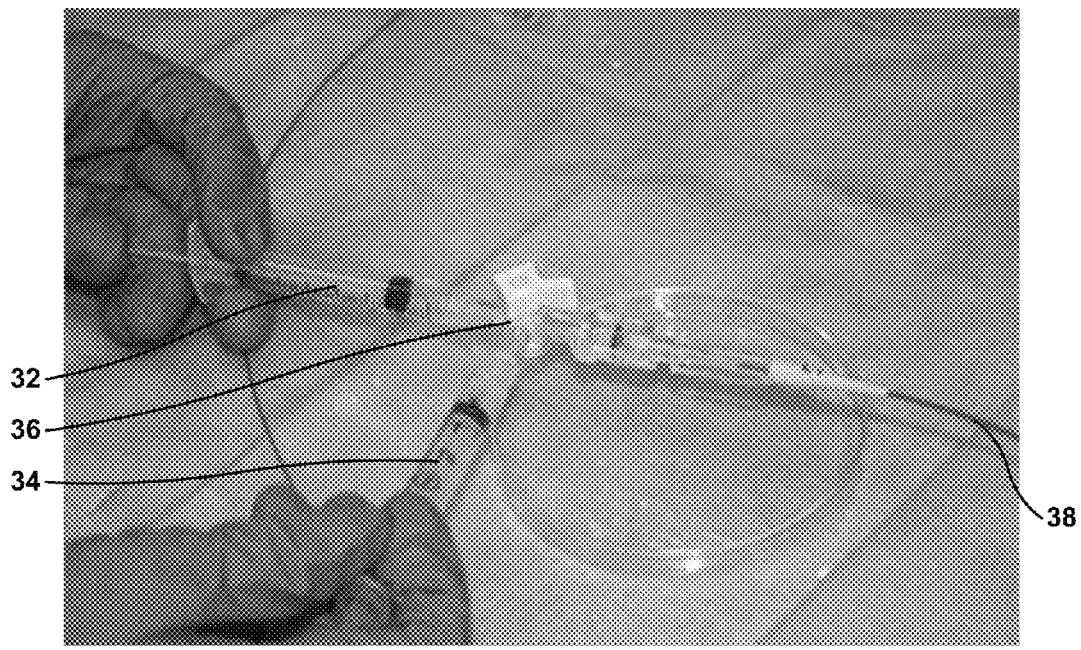
FIGS. 10A-10D are example images of a hydrogel precursor mixture being dispensed through a microcatheter.

FIGS. 10A-10D are example images of a hydrogel precursor mixture being dispensed through a microcatheter. FIG. 10A illustrates a first syringe 32 that contains a first solution. The first solution may include a first solvent and CCN. As described above, the CCN may be present in the first solution at a concentration between about 1.2% w/v and about 2.5% w/v, such as between about 1.5% w/v and about 2.0% w/v, about 1.5% w/v, 1.8% w/v, or 2.0% w/v. The first solvent may include distilled water, saline, or PBS.

FIG. 10A also illustrates a second syringe 34. Second syringe 34 contains a second solution. The second solution may include a second solvent and OCMC. The OCMC may be present in the second solution at a concentration between about 1.0% w/v and about 2.5% w/v, such as between about 1.2% w/v and about 2.5% w/v, between about 1.2% w/v and about 2.0% w/v, between about 1.5% w/v and about 2.5% w/v, between about 1.5% w/v and about 2.0% w/v, about 1.5% w/v, about 1.8% w/v, or about 2% w/v. The second solvent may include distilled water, saline, or PBS. The second solvent may be the same as the first solvent or may be different than the first solvent. Similarly, the concentration of CCN in the first solution may be the same as the concentration of OCMC in the second solution or may be different than the concentration of OCMC in the second solution.

FIG. 10A further illustrates a three-way stopcock 36, which may be used to mix the first solution and the second solution. For example, the valve of three-way stopcock 36 may be manipulated to allow solution to be transferred from first syringe 32 to second syringe 34, from second syringe 34 to first syringe 32, from first syringe 32 to microcatheter 38, or from second syringe 34 to microcatheter 38. By transferring solution from first syringe 32 to second syringe 34 and back, the first and second solutions may be mixed to form a hydrogel precursor mixture. In some examples, the hydrogel precursor mixture be substantially homogeneous, e.g., may consist essentially of a single liquid phase. As described above, in some instances, the hydrogel precursor mixture can additionally include contrast and/or at least one drug.

Figure 10B:
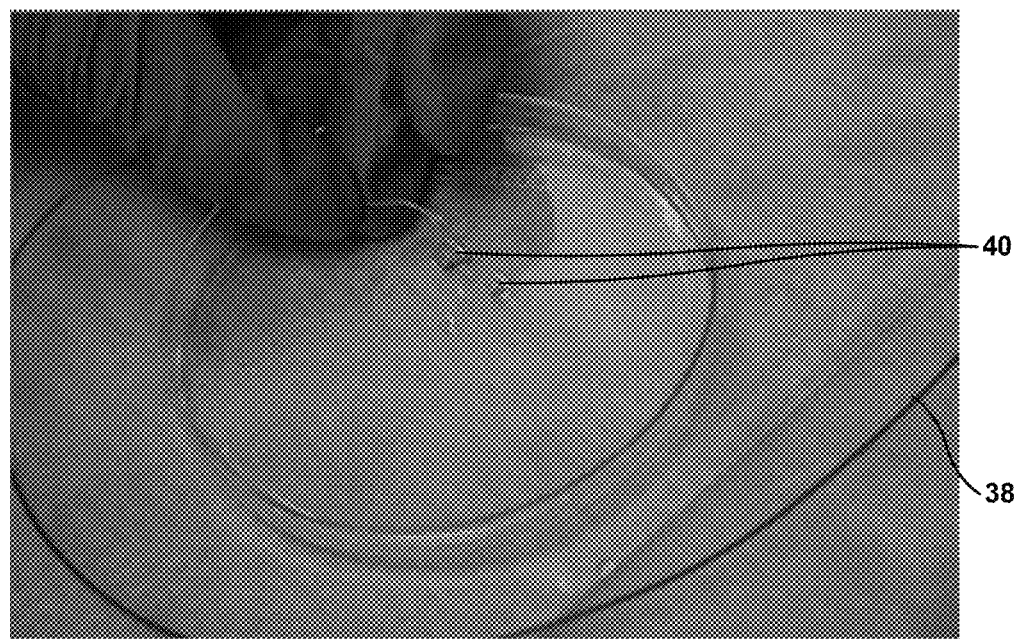
Figure 10C:
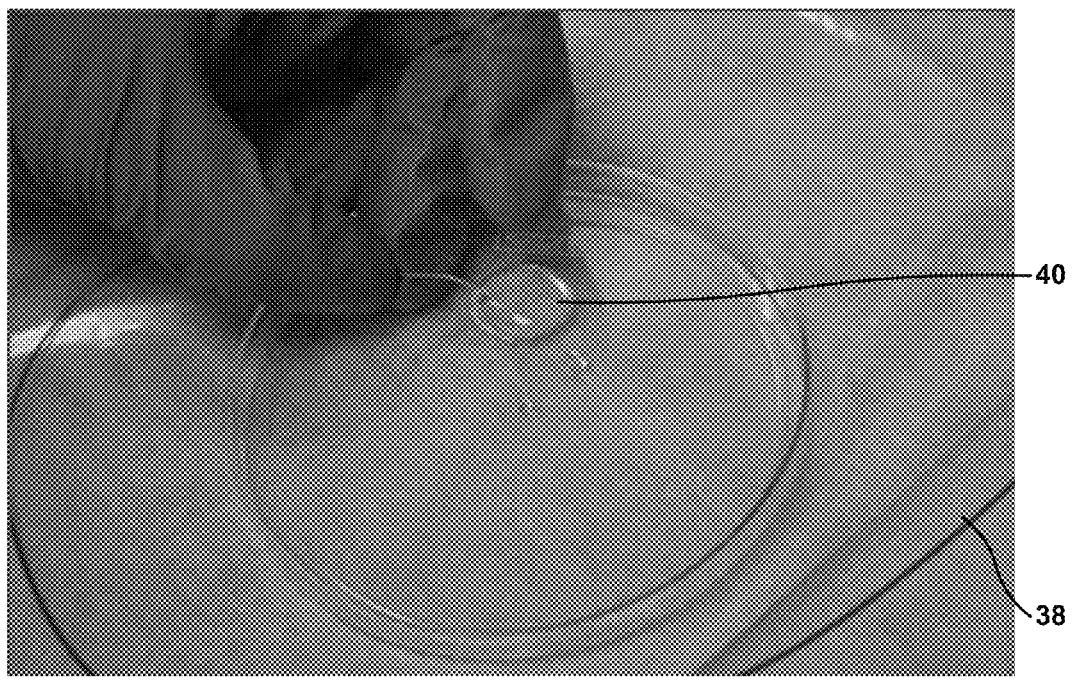

Once the first and second solutions have been mixed to form the hydrogel precursor mixture, the hydrogel precursor mixture may be dispensed through microcatheter 38 from first and/or second syringes 32 and 34 by manipulating the valve of three-way stopcock 36 in the appropriate position. FIGS. 10B and 10C show the hydrogel precursor solution being dispensed into a plastic dish from microcatheter 38.

Figure 10D:
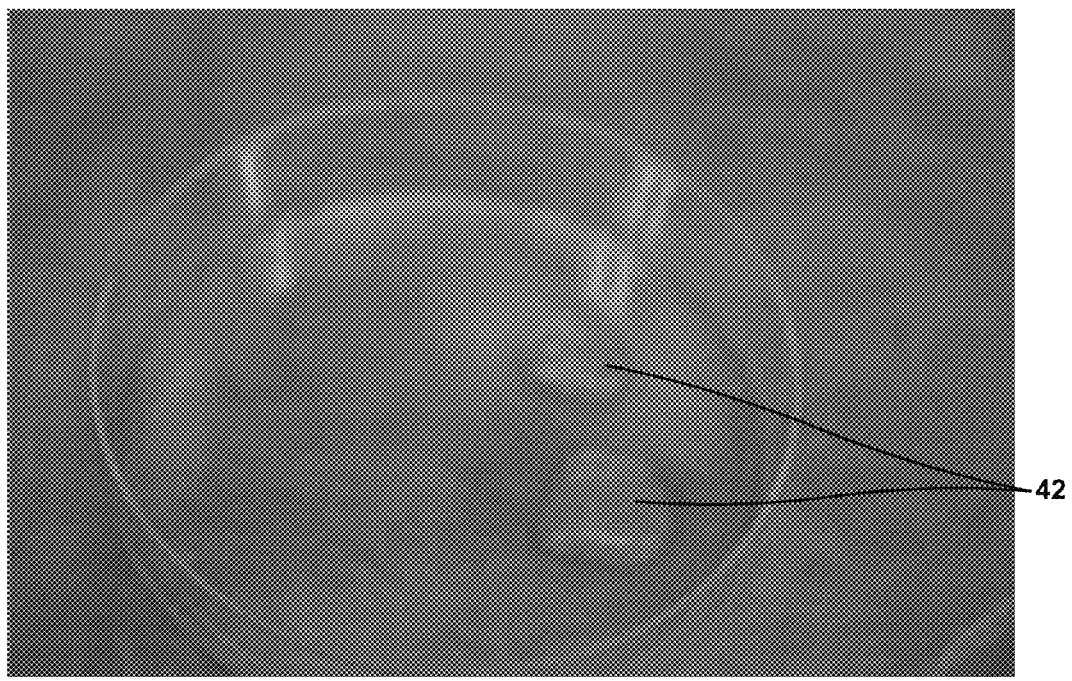

After sufficient time, which may depend at least in part upon a concentration of the OCMC and CCN, a temperature of the hydrogel precursor solution, and/or the first and second solvents, the OCMC and CCN react to form a hydrogel embolic material 42, shown in FIG. 10D.

Hydrogel embolic materials comprising CCN crosslinked with CMC have been described. As described, the hydrogel embolic materials that can be formed by in situ gelation of CCN and OCMC may be used in a variety of applications, including applications for which solid or pre-gelled embolic materials, such as embolic microspheres, are less suited. For example, because the embolic hydrogel is introduced into the human body in liquid form before gelling in vitro, the liquid may advance further distally into a blood vessel, e.g., to portions of the blood vessel that have smaller cross-sectional areas, compared to embolic materials that are injected into the vessel as an already-formed gel or solid (e.g., embolic microspheres). As another example, the embolic hydrogel may be used to fill a cavity within a body of a patient. The embolic hydrogel may be used in application such as adjunct prevention of endoleakage of abdominal aortic aneurysm (AAA) or as a sclerosing agent to treat lymphocele, varicose vein, or pleural effusion. In some examples, the embolic hydrogel can be loaded with contrast material and/or at least one drug to serve as a radiopaque marker and/or a drug delivery vehicle.

Various examples have been described. These and other examples are within the scope of the following claims.

The invention claimed is:

1. A liquid embolic material consisting essentially of a single, substantially homogeneous liquid phase comprising a mixture of a first solution comprising between about 1.2% and about 2.5% weight per volume (w/v) carboxymethyl chitosan (CCN) in a first solvent and a second solution comprising between about 1.2% and about 2.5% w/v oxidized carboxymethyl cellulose (OCMC) in a second solvent.

2. The liquid embolic material of claim 1, wherein the single, substantially homogeneous liquid phase further comprises a contrast material.

3. The liquid embolic material of claim 1, wherein the single, substantially homogeneous liquid phase further comprises a drug.

4. The liquid embolic material of claim 3, wherein the drug comprises at least one of doxorubicin or tetracycline.

5. The liquid embolic material of claim 1, wherein at least one of the first solvent or the second solvent comprises at least one of saline, water, or phosphate buffered saline.

6. The liquid embolic material of claim 1, wherein the first solvent and the second solvent are the same.

7. The liquid embolic material of claim 1, wherein the first solvent and the second solvent are different.

8. The liquid embolic material of claim 1, wherein the liquid embolic material is essentially free of a small molecule crosslinking agent.

9. The liquid embolic material of claim 1, wherein both the first and second solutions have a concentration of about 1.5% w/v CCN and OCMC respectively, wherein the concentrations of CCN and OCMC are sufficient to cause the liquid embolic material to form a crosslinked hydrogel within about 10 minutes after forming the mixture.

10. The liquid embolic material of claim 1, wherein both the first and second solutions have a concentration of about 1.8% w/v CCN and OCMC respectively, wherein the concentrations of CCN and OCMC are sufficient to cause the liquid embolic material to form a crosslinked gel within about 5 minutes after forming the mixture.

11. The liquid embolic material of claim 1, wherein both the first and second solutions have a concentration of about 2% w/v CCN and OCMC respectively, wherein the concentrations of CCN and OCMC are sufficient to cause the liquid embolic material to form a crosslinked gel within about 2 minutes after forming the mixture.

12. The liquid embolic material of claim 1, wherein the first solution comprises between about 1.5% and about 2.0% w/v CCN in the first solvent.

13. The liquid embolic material of claim 1, wherein the second solution comprises between about 1.5% and about 2.0% w/v OCMC in the second solvent.

14. A kit comprising:
a first container containing a first solution comprising a first solvent and between about 1.2% and about 2.5% weight per volume (w/v) carboxymethyl chitosan (CCN);
a second container containing a second solution comprising a second solvent and between about 1.2% and about 2.5% w/v oxidized carboxymethyl cellulose (OCMC); and
a mixing device configured to accept the first solution from the first container, accept the second solution from the second container, and mix the first and second solutions to form a liquid embolic material consisting essentially of a single, substantially homogeneous liquid phase including the first solution and the second solution.

15. The kit of claim 14, wherein the mixing device comprises a three-way stopcock.

16. The kit of claim 14, further comprising a dispensing apparatus, wherein the dispensing apparatus comprises a microcatheter.

17. The kit of claim 16, wherein the dispensing apparatus further comprises at least one of the first container or the second container, and wherein the at least one of the first container or the second container comprises a syringe.

18. The kit of claim 14, wherein at least one of the first container or the second container comprises a syringe.

19. The kit of claim 14, wherein at least one of the first solvent or the second solvent comprises at least one of distilled water, saline, or phosphate-buffered saline.

20. The kit of claim 14, wherein the first solution comprises between about 1.5% and about 2.0% w/v CCN in the first solvent.

21. The kit of claim 14, wherein the second solution comprises between about 1.5% and about 2.0% w/v OCMC in the second solvent.

22. A method of making an embolic hydrogel material, the method comprising:

mixing a first solution comprising between about 1.2% and about 2.5% weight per volume (w/v) carboxymethyl chitosan (CCN) in a first solvent and a second solution comprising between about 1.2% and about 2.5% w/v oxidized carboxymethyl cellulose (OCMC) in a second solvent to form a hydrogel precursor material consisting essentially of a single, substantially homogeneous liquid phase; and allowing the CCN and the OCMC to react to form the hydrogel material.

23. The method of claim 22, further comprising mixing at least one of contrast material or a drug into at least one of the first solvent or the second solvent.

24. The method of claim 22, wherein at least one of the first solvent or the second solvent comprises at least one of saline, distilled water, or phosphate-buffered saline.

25. The method of claim 22, wherein allowing the CCN and the OCMC to react to form the hydrogel material comprises exposing the hydrogel precursor material to a temperature between about 23° C. and about 37° C.

26. A method comprising:

mixing a first solution comprising between about 1.2% and about 2.5% weight per volume (w/v) carboxymethyl chitosan (CCN) in a first solvent and a second solution comprising between about 1.2% and about 2.5% w/v oxidized carboxymethyl cellulose (OCMC) in a second solvent to form a hydrogel precursor material consisting essentially of a single, substantially homogeneous liquid phase;

introducing the hydrogel precursor material to a targeted embolization location within a body of a patient; and allowing the CCN and the OCMC to react to form the hydrogel material and embolize the targeted embolization location.

27. The method of claim 26, further comprising mixing at least one of contrast material or a drug into at least one of the first solvent or the second solvent.

28. The method of claim 26, wherein at least one of the first solvent or the second solvent comprises at least one of saline, distilled water, or phosphate-buffered saline.

29. The method of claim 26, wherein introducing the hydrogel precursor material to a targeted embolization location within a body of a patient comprises introducing the hydrogel precursor material to the targeted embolization location within the body of the patient using a microcatheter.

* * * * *